United States Patent
Sun et al.

(10) Patent No.: US 11,393,092 B2
(45) Date of Patent: Jul. 19, 2022

(54) MOTION TRACKING AND STRAIN DETERMINATION

(71) Applicant: SHANGHAI UNITED IMAGING INTELLIGENCE CO., LTD., Shanghai (CN)

(72) Inventors: Shanhui Sun, Lexington, MA (US); Hanchao Yu, Champaign, IL (US); Qiaoying Huang, Edison, NJ (US); Zhang Chen, Brookline, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 98 days.

(21) Appl. No.: 17/070,705

(22) Filed: Oct. 14, 2020

(65) Prior Publication Data

US 2021/0158543 A1    May 27, 2021

Related U.S. Application Data

(60) Provisional application No. 62/941,198, filed on Nov. 27, 2019.

(51) Int. Cl.
*G06T 7/00*          (2017.01)
*G06T 7/11*          (2017.01)
(Continued)

(52) U.S. Cl.
CPC .......... *G06T 7/0012* (2013.01); *A61B 5/0044* (2013.01); *A61B 5/1128* (2013.01);
(Continued)

(58) Field of Classification Search
CPC ........ G16H 30/40; G16H 50/20; G16H 50/30; G06T 2207/10081; G06T 2207/10088; G06T 2207/10104; G06T 2207/10121; G06T 2207/10132; G06T 2207/30016; G06T 7/0016; G06T 7/254; G06T 7/30; G06T 7/49; G06T 11/206; G06T 13/80;
(Continued)

(56) References Cited

U.S. PATENT DOCUMENTS

2015/0094584 A1*  4/2015  Abe ................... A61B 8/483
                                                        600/443
2016/0098833 A1*  4/2016  Tsadok ............. G06K 9/6201
                                                        382/128

OTHER PUBLICATIONS

Vigneault, Davis M. et al.; "Feature Tracking Cardiac Magnetic Resonance via Deep Learning and Spline Optimization," Institute of Biomedical Engineering, Department of Engineering, University of Oxford. <arXiv:1704.03660v1> (Apr. 2017).
(Continued)

*Primary Examiner* — Manuchehr Rahmjoo
(74) *Attorney, Agent, or Firm* — Zhong Law, LLC

(57) ABSTRACT

Described herein are systems, methods and instrumentalities associated with motion tracking and strain determination. A motion tracking apparatus as described herein may track the motion of an anatomical structure from a source image to a target image and determine corresponding points on one or more surfaces of the anatomical structure in both the source image and the target image. Using these surface points, the motion tracking apparatus may calculate one or more strain parameters associated with the anatomical structure and provide the strain parameters for medical diagnosis and/or treatment.

20 Claims, 11 Drawing Sheets

(51) Int. Cl.

| | |
|---|---|
| G06K 9/62 | (2022.01) |
| G06N 3/04 | (2006.01) |
| G16H 50/50 | (2018.01) |
| G16H 50/30 | (2018.01) |
| G16H 30/40 | (2018.01) |
| G06F 3/0485 | (2022.01) |
| G06T 11/20 | (2006.01) |
| G06T 13/80 | (2011.01) |
| G06T 19/00 | (2011.01) |
| G06T 7/55 | (2017.01) |
| G06T 7/73 | (2017.01) |
| G06T 7/246 | (2017.01) |
| A61B 5/00 | (2006.01) |
| A61B 5/11 | (2006.01) |
| G06T 3/00 | (2006.01) |
| G06N 3/08 | (2006.01) |

(52) U.S. Cl.
CPC .......... *A61B 5/7264* (2013.01); *G06F 3/0485* (2013.01); *G06K 9/6267* (2013.01); *G06N 3/0454* (2013.01); *G06N 3/08* (2013.01); *G06T 3/0093* (2013.01); *G06T 7/0014* (2013.01); *G06T 7/11* (2017.01); *G06T 7/248* (2017.01); *G06T 7/55* (2017.01); *G06T 7/73* (2017.01); *G06T 11/206* (2013.01); *G06T 13/80* (2013.01); *G06T 19/00* (2013.01); *G16H 30/40* (2018.01); *G16H 50/30* (2018.01); *G16H 50/50* (2018.01); *G06T 2200/24* (2013.01); *G06T 2207/10016* (2013.01); *G06T 2207/20081* (2013.01); *G06T 2207/20084* (2013.01); *G06T 2207/30048* (2013.01); *G06T 2210/41* (2013.01)

(58) Field of Classification Search
CPC ................. G06T 19/00; G06T 2200/24; G06T 2207/10016; G06T 2207/10072; G06T 2207/20081; G06T 2207/20084; G06T 2207/30048; G06T 2210/41; G06T 3/0093; G06T 7/0012; G06T 7/0014; G06T 7/11; G06T 7/12; G06T 7/248; G06T 7/55; G06T 7/62; G06T 7/73; A61B 5/0044; A61B 5/1128; G06K 9/6271

See application file for complete search history.

(56) References Cited

OTHER PUBLICATIONS

Qin, Chen et al.; "Joint Learning of Motion Estimation and Segmentation for Cardiac MR Image Sequences," Department of Computing, Imperial College London. <arXiv:1806.04066v1> (Jun. 2018).

Zheng, Qiao et al.; "Explainable cardiac pathology classification on cine MRI with motion characterization by semi-supervised learning of apparent flow," Université Côte d'Azur, Inria, France. <arXiv:1811.03433v2> (Mar. 2019).

Harrild, David M. et al.; "Comparison of Cardiac MRI Tissue Tracking and Myocardial Tagging for Assessment of Regional Ventricular Strain," Int J Cardiovasc Imaging. vol. 28(8) (Dec. 2012).

* cited by examiner

MOTION TRACKING AND STRAIN DETERMINATION

CROSS-REFERENCE TO RELATED APPLICATIONS

This application claims the benefit of Provisional U.S. Patent Application No. 62/941,198, filed Nov. 27, 2019, the disclosure of which is incorporated herein by reference in its entirety.

BACKGROUND

The motion of a human anatomical structure can provide valuable insight into the health of the structure. For instance, cardiac motion can be used to calculate subject-specific muscular strain of the myocardium and facilitate the treatment of multiple cardiac diseases. As an example, patients with dilated cardiomyopathy (DCM) may have a smaller peak global strain compared to normal cases and patients with systolic heart failure may have a smaller strain value in one or more specific regions of the myocardium. The time-varying motion of an anatomical structure such as the myocardium may be tracked using computer-aided technologies and tagged images of the anatomical structure. These techniques may suffer, however, due low resolutions of the images and may require manual labelling of a large number of feature points in the images. Consequently, the number of feature points that may be tracked using these conventional techniques may be limited. The accuracy of the motion tracking may also be unsatisfactory. Therefore, it is desirable to improve these conventional motion tracking techniques to enhance the accuracy and precision of motion tracking as well as strain determination while also reduce the amount of manual work required to complete the tasks.

SUMMARY

Described herein are neural network-based systems, methods and instrumentalities associated with motion tracking and strain determination. A motion tracking apparatus as described herein may comprise one or more processors. The one or more processors may be configured to obtain a source image and a target image of an anatomical structure (e.g., a myocardium) and determine, based on the source image and the target image, a motion field that indicates a motion (e.g., changes in position and/or shape) of the anatomical structure from the source image to the target image. The one or more processors may be further configured to determine, in a source image, a first plurality of points located on a first surface (e.g., a first boundary) of the anatomical structure and a second plurality of points located on a second surface (e.g., a second boundary) of the anatomical structure that corresponds to the first plurality of points. The correspondence between the first and second pluralities of points may be established, for example, using a partial differential equation such as Laplace's equation. Once the first and second pluralities of points are determined in the source image, the one or more processors of the motion tracking apparatus may estimate respective locations of those points in the target image based on the locations of the points in the source image and the motion field that indicates the motion of the anatomical structure from the source image to the target image. The one or more processors may calculate one or more strain parameters associated with the anatomical structure based on the respective locations of the first plurality of points and the second plurality of points in the source image and the respective locations of the first plurality of points and the second plurality of points in the target image.

The correspondence between the first plurality of points and the second plurality of points may be established by solving Laplace's equation to obtain one or more equal-potential surfaces, where each of the one or more equal-potential surfaces may comprise at least one point among the first plurality of points and at least one point among the second plurality of points. The first surface of the anatomical structure described herein may comprise an inner surface or an inner layer of the anatomical structure (e.g., an endocardium) while the second surface of the anatomical structure may comprise an outer surface or an outer layer of the anatomical structure (e.g., an epicardium).

The motion tracking apparatus may determine the motion field using one or more artificial neural networks and the determination may comprise deriving a first motion field (e.g., a coarse motion field) based on features extracted from the source image and the target image, and refining the first motion field to obtain a refined motion field. The refinement of the coarse motion field may be performed by at least deriving a warped image based on the source image and the coarse motion field, determining a second motion field based on features extracted from the warped image and the target image, and combining (e.g., aggregating) the first and the second motion fields.

The source and target images of the anatomical structure described herein may comprise respective source and target segmentation masks of the anatomical structure. The one or more strain parameters determined by the motion tracking apparatus may include a radial strain, a circumferential strain, a regional strain, a strain rate, etc. The strain values may be determined, for example, based on distances between corresponding points on one or more surfaces of the anatomical structure. For instance, to determine a radial strain, the motion tracking apparatus may determine, in the source image of the anatomical structure, a first distance between a first point on a first surface of the anatomical structure and a second point on a second surface of the anatomical structure. The motion tracking apparatus may further determine, in the target image, a second distance between the first point on the first surface of the anatomical structure and the second point on the second surface of the anatomical structure. The radial strain may then be calculated based a change between the first distance and the second distance.

Similarly, to determine a circumferential strain, the motion tracking apparatus may determine, in the source image, a first projection of the radial distance between corresponding first and second points located on the first and second surfaces of the anatomical structure in a circumferential direction of the anatomical structure. The motion tracking apparatus may further determine, in the target image, a second projection of the distance between the first and second points in the circumferential direction of the anatomical structure. The motion tracking apparatus may then calculate the circumferential strain based on a change between the first and second projections of the radial distance. The distances and/or changes in the distances may be represented, for example, by respective vectors and/or vector changes.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings. Embodiments may be described herein using one or more specific human anatomical structures such as the human heart (e.g., a myocardium) and/or one or more types of imagery data (e.g., certain types of images and/or videos) as examples, but it should be noted that the techniques disclosed herein are not limited to the example anatomical structures or imagery data, and can be used to estimate and track the motion and deformation of other anatomical structures as well.

Figure 1:
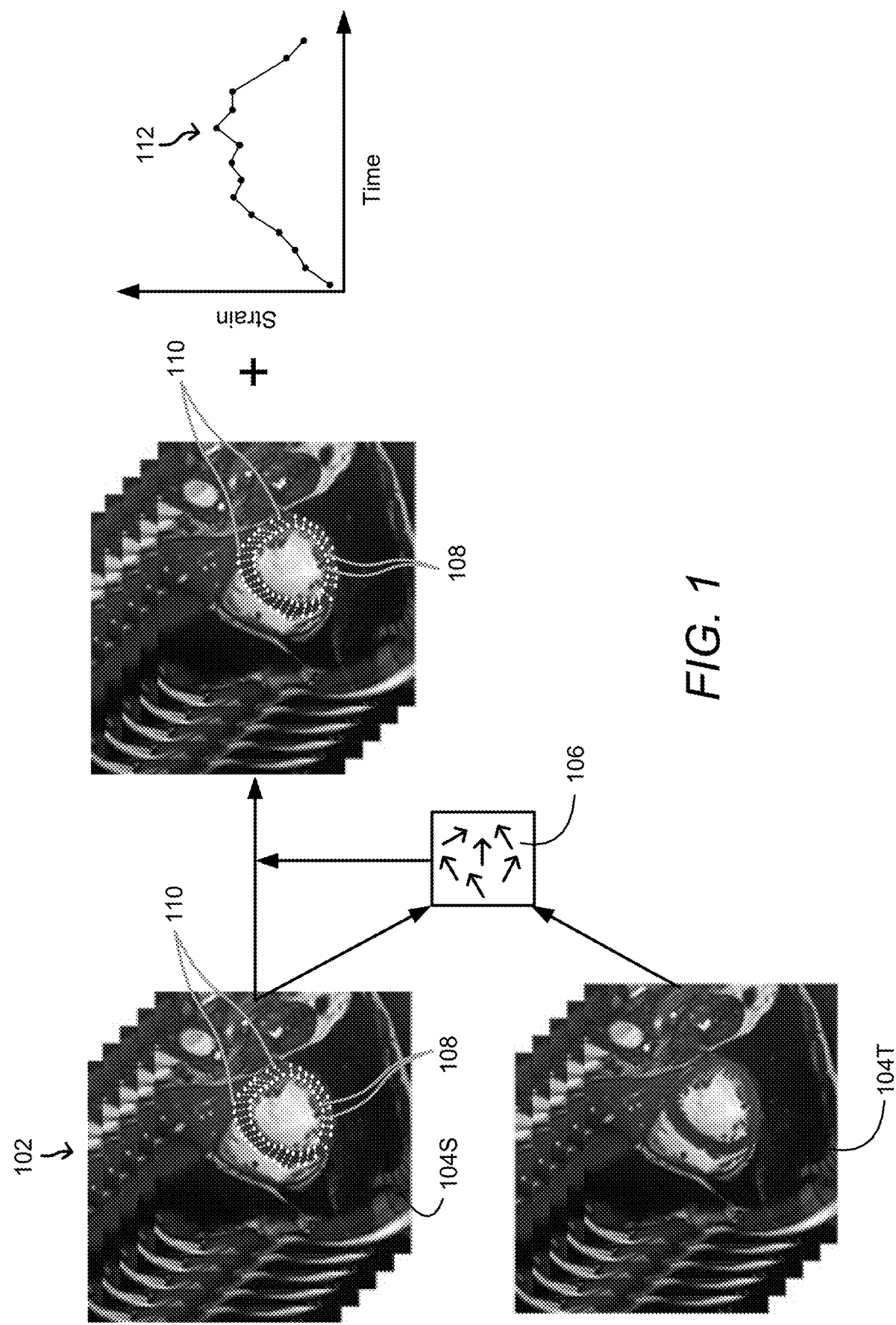
FIG. 1 is a block diagram illustrating an example of motion tracking and strain determination.

FIG. 1 is a block diagram illustrating an example of using a motion tracking apparatus described herein to track the motion of a human anatomical structure such as a myocardium and estimate the strain (e.g., deformation) of the myocardium based on the tracked motion. As shown, the motion tracking apparatus may perform the tracking (e.g., estimation) based on imagery of the myocardium such as a magnetic resonance imaging (MRI) video 102 of the heart (e.g., a cardiac cine MRI). The video 102 may comprises multiple images of the myocardium recorded at different points in time (e.g., sequential points along a time axis t) and the corresponding time period may span one or more cardiac cycles. For example, the video 102 may comprise images that depict the motion of the myocardium starting from relaxation to contraction and then back to relaxation. As such, the motion tracking apparatus may, starting from a source image 104S of the video 102, estimate the motion of the myocardium between the source image 104S and a target image 104T by comparing the two images and identifying changes that have occurred between the time the source image 104S is recorded and the time the target image 104T is recorded. The motion tracking apparatus may then use the target image 104T as a new source frame and repeat the tracking process for the other images of the video 102 to track the motion of the myocardium for one or more full cardiac cycles.

The motion described herein may be represented by a motion field 106 generated by the motion tracking apparatus. Such a motion field may be a dense motion field and may include a vector field, a grid of vectors, a vector-value function, a map, and/or the like that indicates or represents respective changes, disparities or displacements of visual features at multiple locations (e.g., at each pixel) of the source image 104S and the target 104T. Further, the motion tracking apparatus may obtain a first plurality of points 108 (e.g., feature points) located on a first surface (e.g., boundary) of the myocardium (e.g., an inner surface of the myocardium or the endocardium) and a second plurality of points 110 located on a second surface (e.g., boundary) of the myocardium (e.g., an outer surface of the myocardium or the epicardium). Each point in the second plurality of points 110 may correspond to a point in the first plurality of points 108 (e.g., indicated by the dotted lines in FIG. 1) such that a respective distance between each pair of corresponding points may indicate a respective thickness of the myocardium. In examples, the first plurality of points 108 and the second plurality of points 110 may be derived using a partial differential equation such that Laplace's equation. The derivation of the corresponding points 106, 108 will be described in greater detail below.

Since the motion field 106 may indicate changes from the source image 104S to the target image 104T, the motion tracking apparatus may determine (e.g., estimate) corresponding locations of the first plurality of points 108 and the second plurality of points 110 in the target image 104T based on the motion field 106 and respective locations of the first plurality of points 108 and the second plurality of points 110 in the source image 104S. For example, the motion tracking apparatus may apply the changes indicated by the motion field 106 with respect to the locations of the first plurality of points 108 and the second plurality of points 110 to the locations of those points in the source image 104S to derive the corresponding locations of the points in the target image 104T. Using the respective locations of the first plurality of points 108 and the second plurality of points 110 in the source image 104S and the target image 104T, the motion tracking apparatus may further determine one or more strain parameters 112 associated with the myocardium. Such strain parameters may include, for example, a radial strain of the myocardium, a circumferential strain of the myocardium, a regional strain of the myocardium, a strain rate of the myocardium, etc. The computation of the one or more strain parameters 112 will be described in greater detail below.

Figure 2:
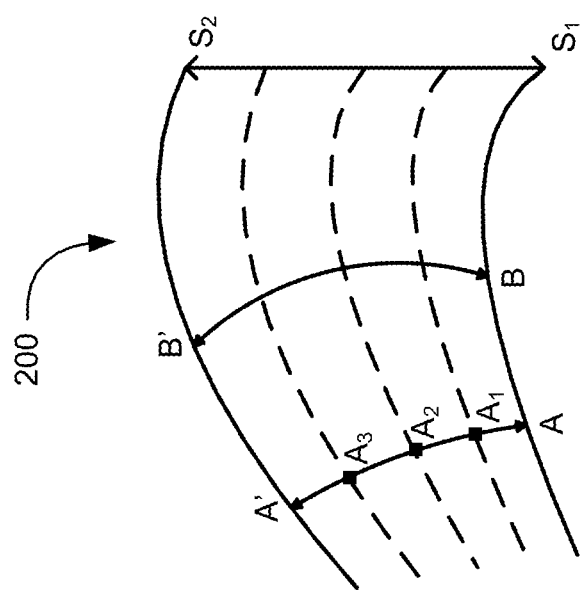
FIG. 2 is a diagram illustrating an example of determining corresponding surface points using Laplace's equation.

As described herein, the motion tracking apparatus may obtain corresponding points on two surfaces of the myocardium using a partial differential equation (PDE) such as Laplace's equation. FIG. 2 is a diagram showing an example of how Laplace's equation may be used to derive these corresponding points. Laplace's equation may be a second-order partial differential equation and may be used to capture (e.g., mathematically) the surface or boundary conditions of an anatomical structure such as the myocardium shown in FIG. 1. For instance, Laplace's equation may be used to compute a scalar field $\psi$ (e.g., representing values of electric potential) enclosed between two boundary contours (e.g., inner and outer surfaces) $S_1$ and $S_2$ of an anatomical structure 200 shown in FIG. 2. The equation may take the following form:

$$\nabla^2 \psi = \frac{\delta^2 \psi}{\delta x^2} + \frac{\delta^2 \psi}{\delta y^2} + \frac{\delta^2 \psi}{\delta z^2} = 0 \qquad 1)$$

where ψ may be equal to $\psi_1$ on $S_1$ and $\psi_2$ on $S_2$. By solving the equation, a layered set of surfaces (e.g., shown by dashed lines in FIG. 2) may be determined that transition from $S_1$ to $S_2$ and respective values of ψ may be defined for one or more points (e.g., any point) between the two surfaces $S_1$ and $S_2$, e.g., A and A', B and B', etc. Points on the inner surface $S_1$ (e.g., such as points A and B) may be assigned a ψ value of 0 (e.g., in units of volts to indicate electric potential), while points on the outer surface $S_2$ (e.g., such as points A' and B') may be assigned a ψ value of 10,000, and points between the two surfaces (e.g., between A and A' or between B and B') may be assigned respective ψ values that satisfy $\nabla'^2 \psi = 0$. This way, non-intersecting (e.g., parallel) intermediate lines may be obtained based on Laplace's equation, for example, using the following formula:

$$E = -\nabla \psi \quad (2)$$

Further, E may be normalized, e.g., based on the following equation, to obtain gradient vectors N that correspond to nested sublayers between $S_1$ to $S_2$:

$$N = E/\|E\| \quad (3)$$

where N may point perpendicularly to the corresponding sublayer.

For simplicity of illustration, FIG. 2 only shows three nested sublayers (e.g., in dashed lines) that may correspond to isopotential values of 2500, 5000, and 7500V. A skilled person in the art will understand, however, that more nested sublayers may be derived in similar manners and once N is determined, a streamline may be computed by starting at a surface point (e.g., A on surface $S_1$) and integrating N (e.g., using the forward Euler integration method) to arrive at a point on the opposite surface (e.g., A' on surface $S_2$). For example, as shown in FIG. 2, a streamline may be determined to reach A' from A through interior points $A_1$, $A_2$ and $A_3$ based on a specific integration step size. And by decreasing the integration step size, more interior points between A and A' may be obtained and the accuracy of locating A' may be increased accordingly. Thus, given a point on a first surface (e.g., $S_1$ or $S_2$) of the anatomical structure 200, a corresponding point may be identified on a second surface (e.g., the opposite surface) of the anatomical structure 200 by solving Laplace's equation.

Figure 3:
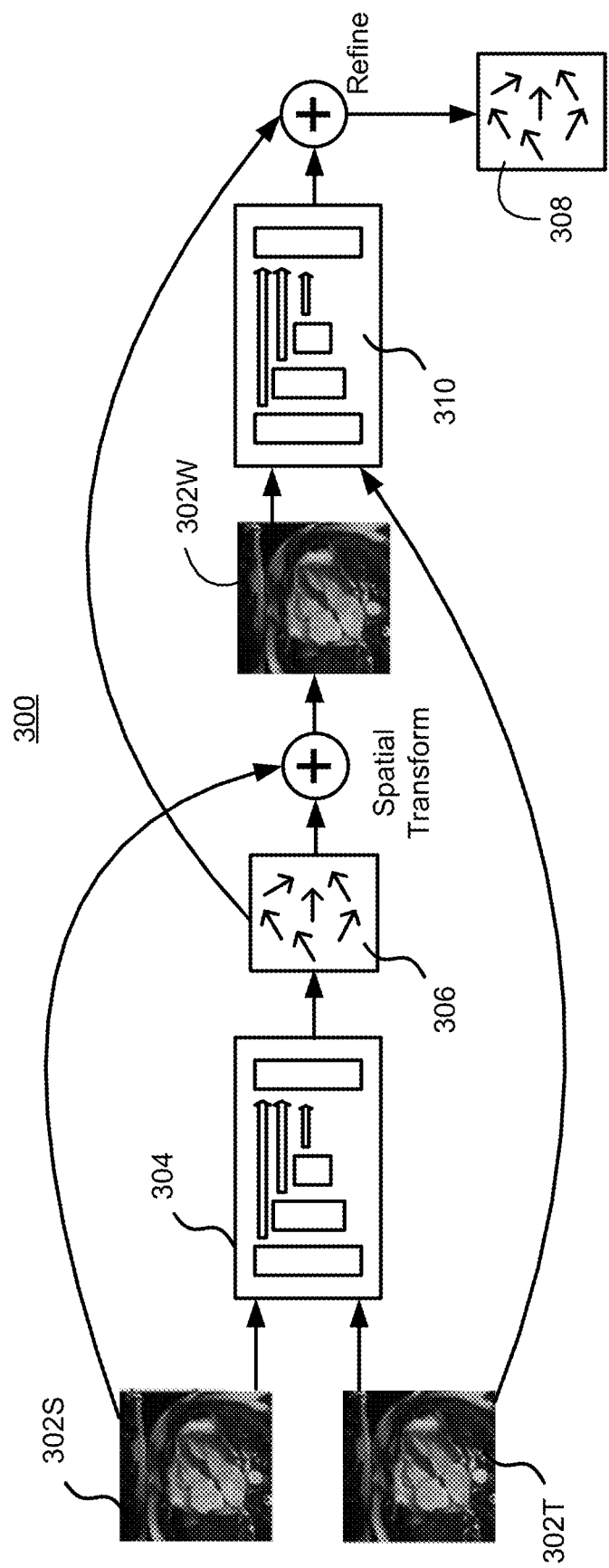
FIG. 3 is a block diagram illustrating an example of motion estimation using a motion tracking apparatus described herein.

Various techniques may be used to estimate the motion field 106 shown in FIG. 1. FIG. 3 illustrates an example of estimating the motion of an anatomical structure (e.g., a myocardium) using a motion tracking apparatus 300 (e.g., the motion tracking apparatus described in association with FIG. 1). As shown, the motion tracking apparatus 300 may obtain (e.g., receive or derive from a cardiac cine MRI) a source image 302S (e.g., the source image 104S in FIG. 1) and a target image 302T (e.g., the target image 104T in FIG. 1) of the anatomical structure. The source image 302S and target image 302T may be captured at different points in time (e.g., at consecutive times along a time axis) and may depict respective states of the anatomical structure at those times. The motion tracking apparatus 300 may comprise an artificial neural network 304 (e.g., a fully convolutional neural network (FCN)) and the artificial neural network 304 may in turn include an encoder and/or a decoder (e.g., arranged as a variational autoencoder). The encoder may include a plurality of layers such as one or more convolutional layers, one or more pooling layers and/or one or more fully connected layers and may be trained to extract features from the source image 302S and the target image 302T, respectively, by performing a series of convolution and down-sampling operations through the layers of the neural network. For example, each of the convolutional layers of the encoder may include a plurality of convolution kernels or filters (e.g., with a kernel size of 3×3 or 5×5) configured to extract specific features from the source image 302S and the target image 302T. The convolution operation may be followed by batch normalization and/or non-linear activation, and the features extracted by the convolutional layers (e.g., in the form of one or more feature maps or feature vectors) may be down-sampled through one or more pooling layers (e.g., using a 2×2 window and a stride of 2) to reduce the redundancy and/or dimension of the features by various factors (e.g., by factors of 2, 4, etc.).

The decoder of the artificial neural network 304 may be configured to receive the respective features extracted from the source image 302S and the target image 304T, analyze (e.g., compare) the features, and generate a motion field 306 (e.g., a flow field) that indicates a change (e.g., motion) of the anatomical structure from the source image 302S to the target image 302T. The decoder may comprise a plurality of layers such as one or more convolutional layers, one or more un-pooling layers, and/or one or more fully connected layers. Through these layers, the decoder may perform a series of up-sampling and/or transposed convolution (e.g., deconvolution) operations on the respective feature extracted by the encoder described herein. For example, the decoder may up-sample the extracted features via the one or more un-pooling layers (e.g., based on pooled indices provided by the encoder) and the one or more convolutional layers (e.g., using 3×3 or 5×5 transposed convolutional kernels and/or a stride of 2) to obtain an up-sampled (e.g., dense) version of the features. The decoder may then derive the motion field 306 based on the up-sampled features. As described herein, the motion field 306 may include a vector field, a grid of vectors, a vector-value function, and/or the like that indicate disparities or displacements of features between the source image 302S and the target image 302T.

The parameters of the neural network 304 (e.g., weights associated with the various filters of the network) may be learned via a training process (e.g., a machine-learning process) that utilizes a loss function (e.g., a loss function based on L2 norms). Through the training, the neural network 304 may acquire the ability to estimate the motion of the anatomical structure in an accurate and smooth manner, for example, by minimizing a Huber loss. To further improve the accuracy and smoothness of the motion estimation, the motion tracking apparatus 300 may be configured to treat the motion field 306 as a first or coarse motion field and perform additional operations to refine the motion indicated by the first motion field 306. These additional operations may include, for example, warping the source image 302S to derive a warped image 302W and determining a second motion field between the warped image 302W and the target image 302T. The second motion field may then be combined with the first motion field 306 (e.g., by aggregating the respective motions indicated in the first and second motion fields) to obtain a refined motion field 308.

The motion tracking apparatus 300 may include a spatial transformation network (e.g., a differentiable spatial transformation network) configured to generate the warped image 302W based on the source image 302S and the coarse motion field 306. The spatial transformation network may include an input layer, one or more hidden layers (e.g., convolutional layers), and/or an output layer. In example operations, the spatial transformation network may take the source image 302S and/or the motion field 306, obtain a plurality of transformation parameters based on the motion field 306, and create a sampling grid including a set of points from which the source image 302S may be sampled to generate the transformed or warped image 302W. The source image 302S and the sampling grid may then be provided to a sampler of the spatial transformation network to produce the warped image 302W, e.g., by sampling from the source image 302S at the grid points.

Responsive to obtaining the warped image 302W, the motion tracking apparatus 300 may determine the motion between the warped image 302W and the target image 302T, for example, via the neural network 304 or a second artificial neural network 310 that may have similar structures and/or parameters as the neural network 304. The determination may be made, for example, using similar techniques as those used to derive the motion field 306, and the motion indicated by the motion field 306 and the additional motion between the warped image 302W and the target image 302T may be combined to derive the refined motion field 308.

Figure 4:
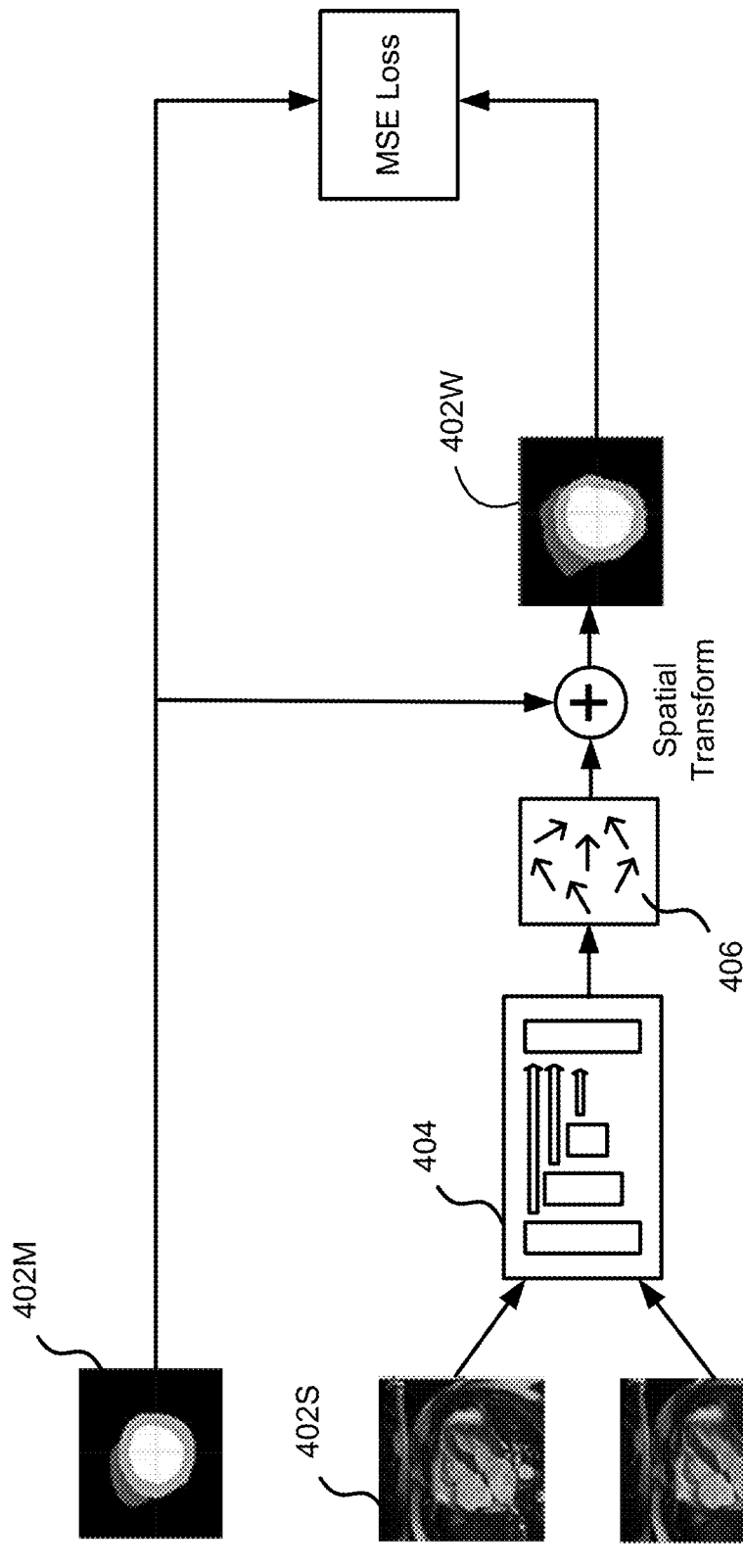
FIG. 4 is a block diagram illustrating an example way of improving the accuracy of motion estimation.

The motion tracking techniques are described herein with reference to an encoder, a decoder, and/or other neural network components or machine-learning techniques. It should be noted, however, that the proposed motion tracking and strain determination systems, methods and apparatus are not limited to using these example components or techniques to perform an intended function and may instead be implemented using other types of neural networks and/or machine-learning models without impacting the efficiency and/or effectiveness of motion tracking and strain determination. For instance, FIGS. 4-7 illustrate various techniques that may be employed to realize and/or improve the functionality of the motion tracking apparatus described herein. As shown in FIG. 4, the training of a motion estimation neural network as described herein may utilize one or more segmentation masks 402M in addition to a source image 402S and a target image 402T to improve the accuracy of the motion estimation. For instance, the one or more segmentation masks 402M may include respective segmentation masks associated with the source image 402S and target image 402T. Upon predicting a motion field 406 via a neural network 404 (e.g., using the techniques described herein), the segmentation mask associated with the source image 402S may be warped based on the motion field 404 to derive a warped mask 402W (e.g. using the spatial transformation techniques described herein). The warped mask 402W may then be compared with the segmentation mask associated with target mask and the difference between the two masks (e.g. determined based on mean squared errors (MSE) between the masks) may be used to tune the parameters of the motion estimation neural network 404.

Figure 5:
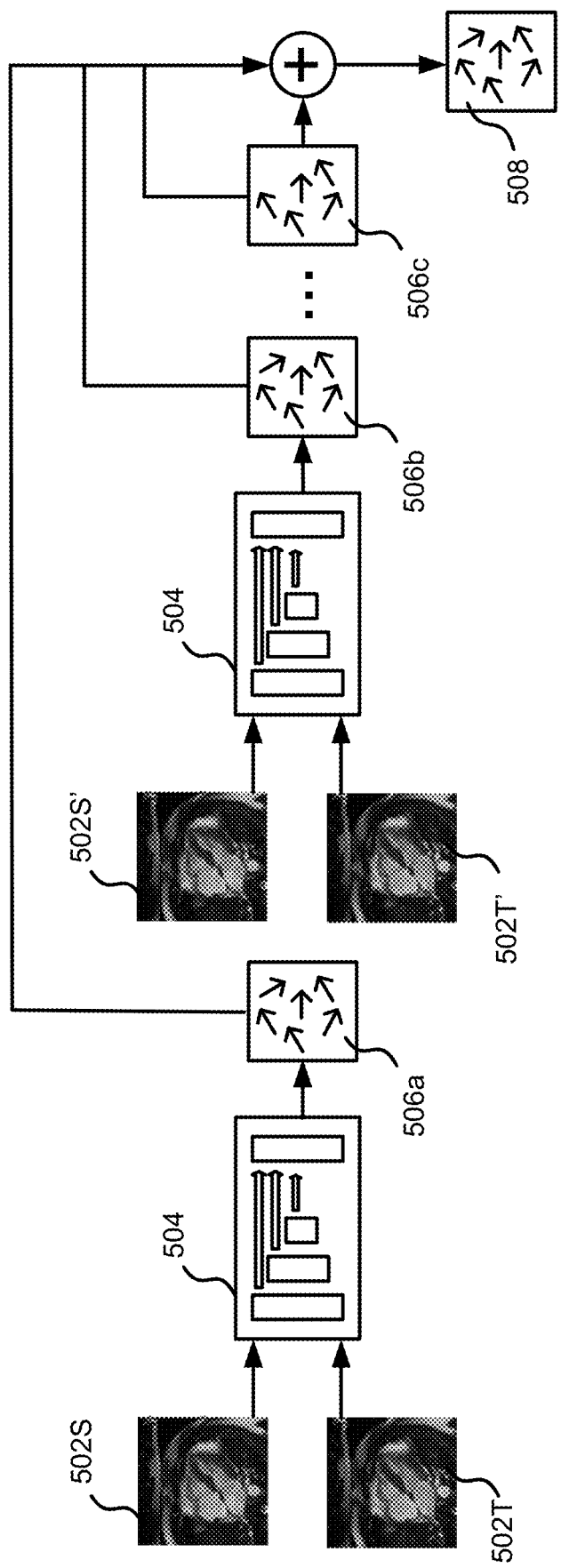
FIG. 5 is a block diagram illustrating an example of frame-by-frame motion estimation.
Figure 6:
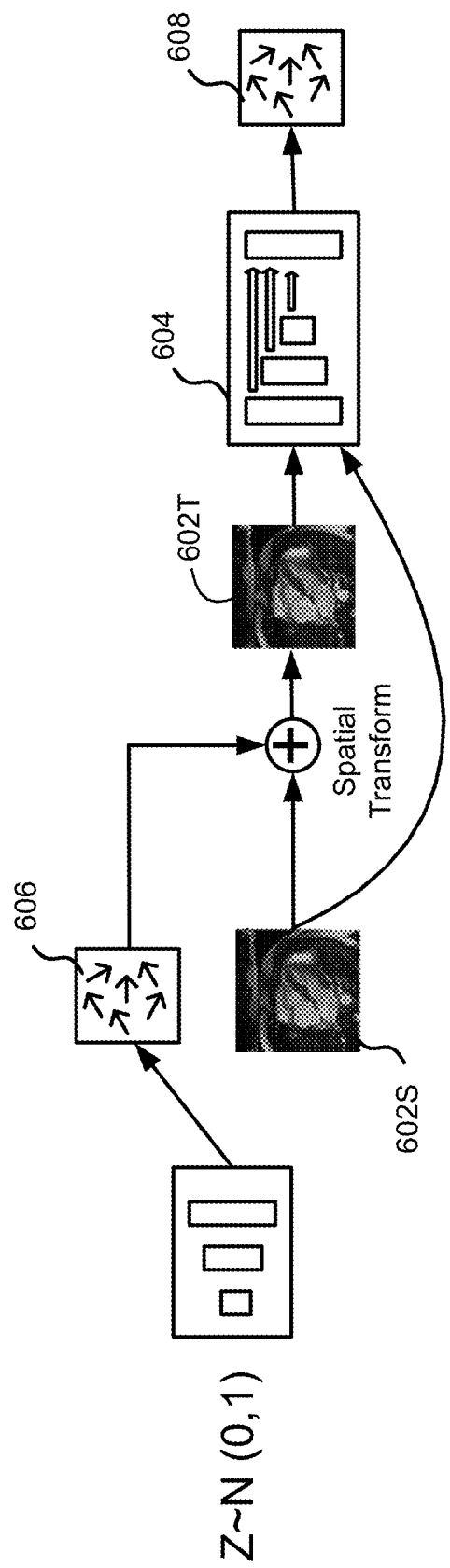
FIG. 6 is a block diagram illustrating an example of direct supervision and/or data augmentation.
Figure 7:
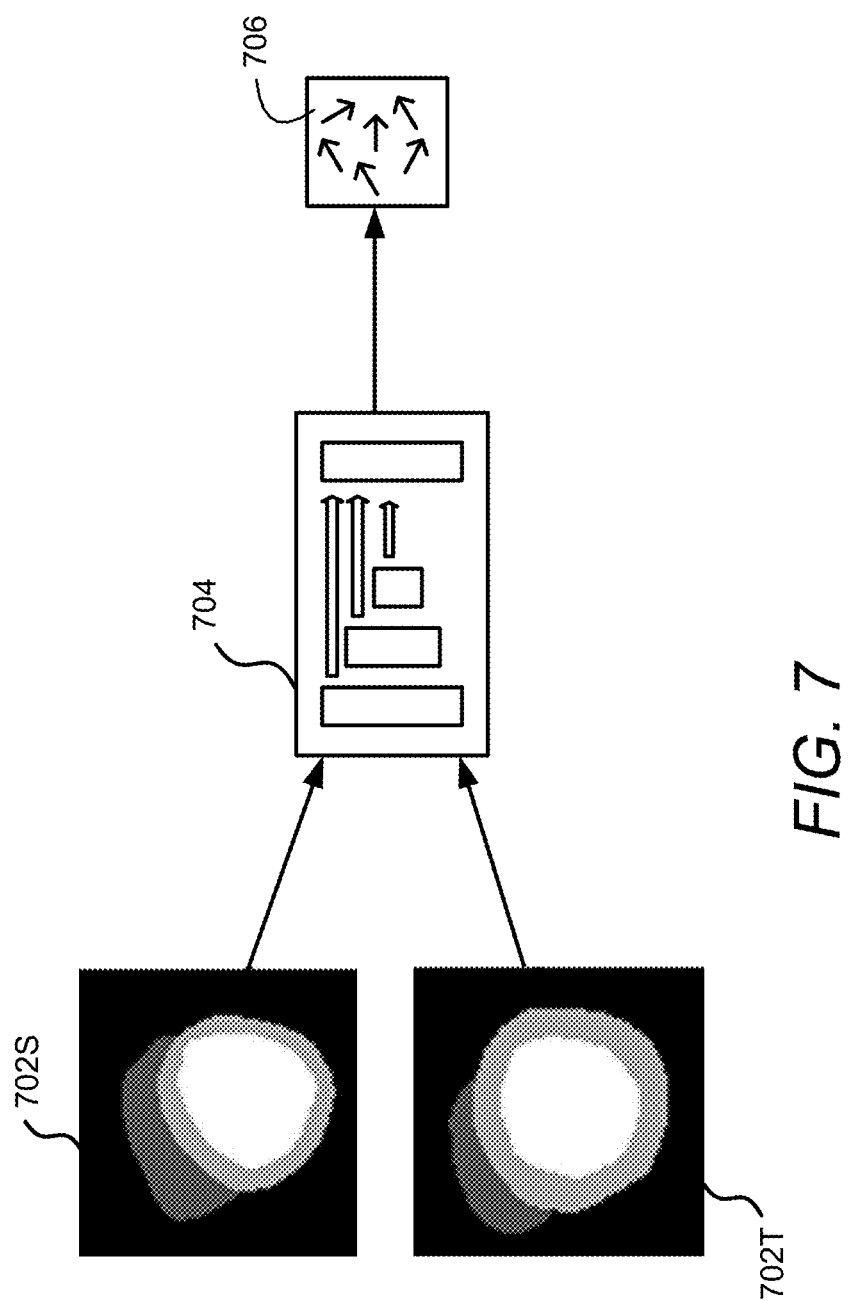
FIG. 7 is a block diagram illustrating an example of predicting a motion field based on the segmentation masks of an anatomical structure.

As another example, FIG. 5 illustrates a frame-by-frame motion estimation technique that may be used to improve the functionality of the motion tracking apparatus described herein. As shown, given a source image 502S and a target image 502T, one or more intermediate motion fields 506a, 506b, etc. may be estimated using a neural network 504 and based on images 502S', 502T', etc. that are between the source image 502S and the target image 502T. The intermediate motion fields may then be combined to obtain a refined motion field 508. As another example, FIG. 6 illustrates a technique that introduces direct supervision and/or data augmentation into the training of a motion estimation network 604. As shown, a motion field 606 may be generated by sampling from a distribution Z~N (0,1). The motion field 606 may then be used to warp (e.g., via spatial transformation) a source image 602S to obtain a target image 602T. Since a ground truth motion field associated with the source image 602S and the target image 602T may be readily available, the training of the motion estimation neural network 604 may be conducted with an objective to minimize the difference (e.g., MSE) between the ground truth motion field and a motion field 608 predicted by the neural network 604. As another example, FIG. 7 illustrates a technique that predicts a motion field based on segmentation masks of an anatomical structure. As shown, a motion estimation neural network 704 may be trained to receive a source segmentation mask 702S associated with an anatomical structure (e.g., a myocardium) and a target segmentation mask 702T associated with the anatomical structure. The segmentation masks may be generated based on images of the anatomical structure, for example, using machine-learned segmentation models. During the training of the neural network 704, the network may estimate a motion field 706 based on the segmentation masks, use the motion field 706 to warp the source segmentation 702S, and adjust the parameters (e.g., weights) of the neural network 704 based on a difference between the warped segmentation mask and the target segmentation mask 702T. In the testing phase, the neural network 704 may receive images that comprise similar segmentation masks as the source segmentation 702S and the target segmentation 702T and track the motion of the anatomical structure by generating a motion field based on the input segmentation masks.

Figure 8:
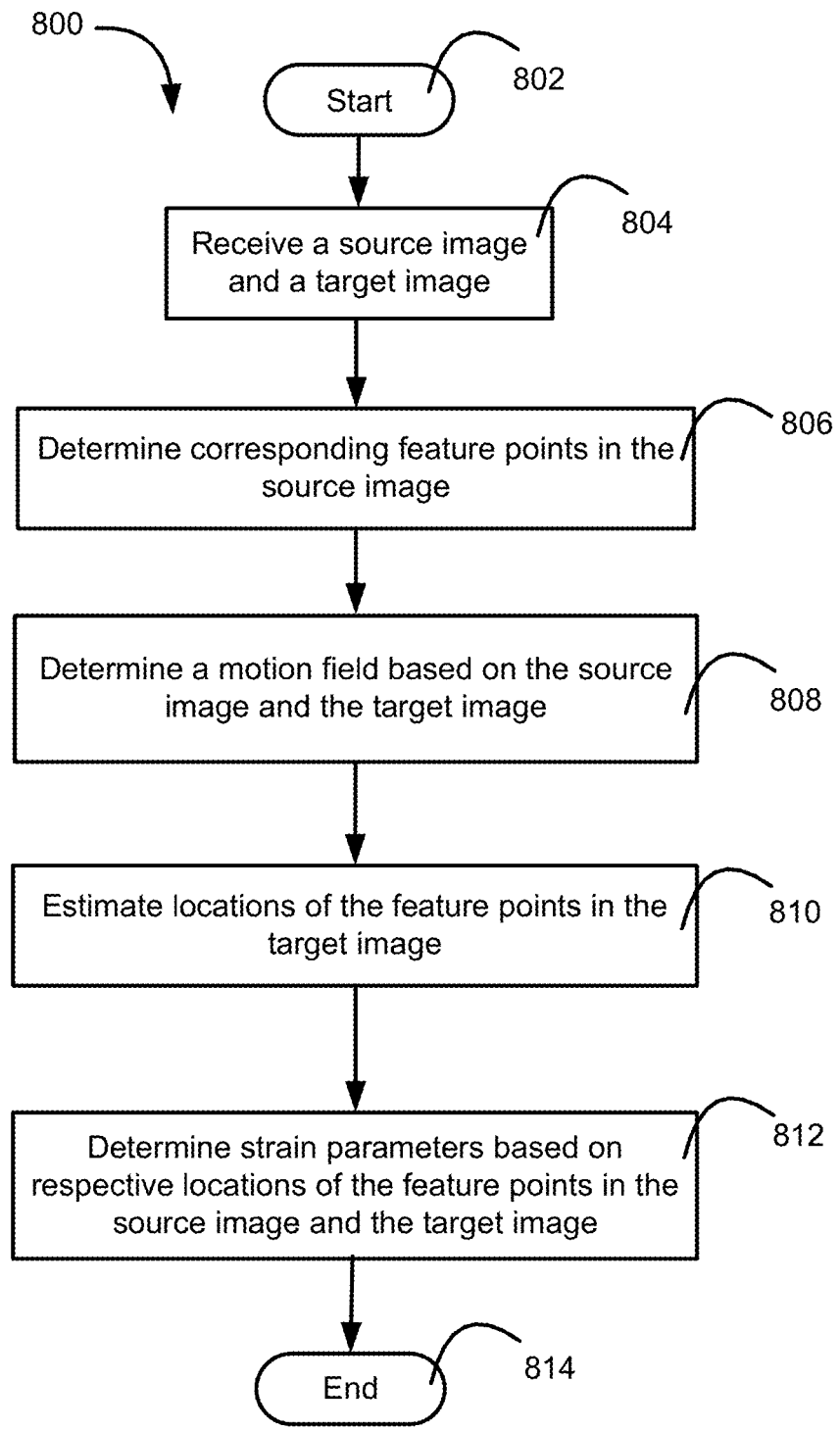
FIG. 8 is a flowing diagram illustrating an example of tracking motion and determining strain values based on the tracked motion.

FIG. 8 shows an example process 800 that may be performed by a motion tracking apparatus described herein to track the motion of an anatomical structure and determine one or more straining parameters associated the anatomical structure based on the tracked motion. As shown, the process 800 may start at 802 and, at 804, the motion tracking apparatus may receive a source image and a target image that depict respective states of the anatomical structure at different points in time. At 806, the motion tracking apparatus may determine corresponding feature points in the source image that are located on the surfaces of the anatomical structure (e.g., the first plurality of points 108 and the second plurality of points 110 shown in FIG. 1). As described herein, these feature points and the correspondence between them may be determined based on a partial differential equation such as Laplace's equation shown in Equation 1 and/or the Euler integration method. At 808, the motion tracking apparatus may determine a motion field based on the source image and the target image that represents a motion of the anatomical structure from the source image to the target image. As described herein, the motion field may be determined using one or more artificial neural networks via a coarse-to-fine estimation process. Upon determining the motion field, the motion tracking apparatus may, at 810, estimate respective locations of the feature points in the target image based on the motion field determined at 808 and the locations of the feature points in the source image. Subsequently, at 812, the motion tracking apparatus may calculate one or more strain parameters (e.g., radial and/or circumferential strains, strain rate, etc.), before exiting the process 800 at 814.

Figure 9A:
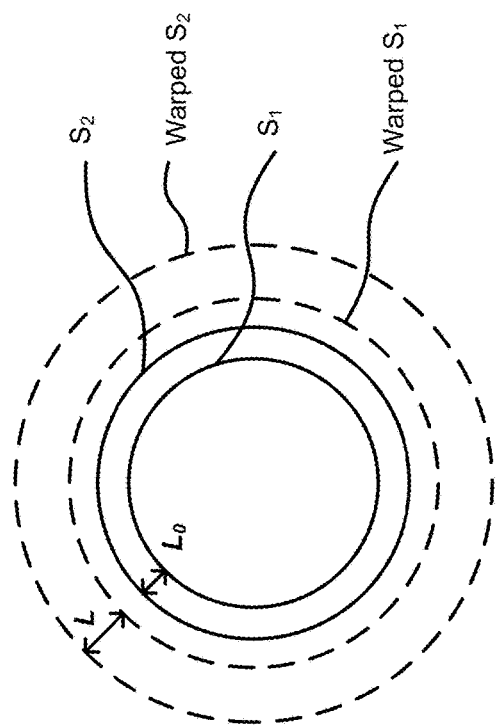
FIGS. 9A-9C are block diagrams illustrating examples of strain value determination.
Figure 9B:
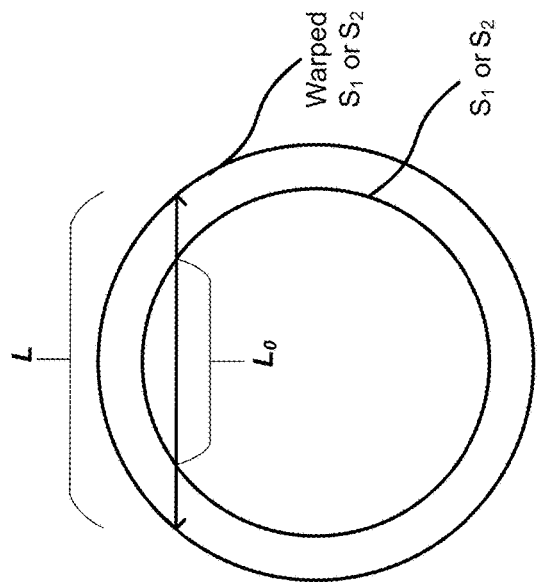
Figure 9C:
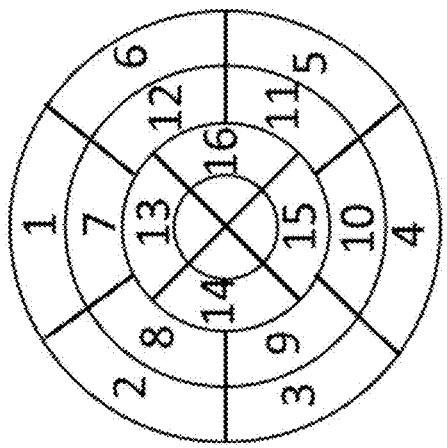

FIGS. 9A-9C shows examples of how a motion tracking apparatus described herein may determine one or more strain parameters based on feature points located on an inner and/or an outer surface of a myocardium. The strain values may be calculated using strain tensors including, e.g., a Green-Lagrange tensor and/or an Engineering tensor. The strain values may be of different types including, e.g., left ventricle (LV) radial, LV epicardium, LV endocardium, right ventricle (RV) strain, etc.

FIG. 9A shows an example of calculating a radial strain. As shown, the motion tracking apparatus may determine, based on a source image of the myocardium, a first (e.g., initial) distance $L_0$ in a radial direction of the myocardium based on two points respectively located on an inner surface $S_1$ and an outer surface $S_2$ of the myocardium. For instance, one of the two points may be a part of the first plurality of points 108 in FIG. 1 and the other one of the two points may be a part of the second plurality of points 110 in FIG. 1. Then, in a target image of the myocardium, the motion tracking apparatus may locate the two points used to calculate the first distance $L_0$ and determine a second distance L between the two points. Due to the motion of the myocardium from the source image to the target image, the surfaces $S_1$ and $S_2$ may have warped in the target image (e.g., indicated by dotted lines in FIG. 9A), so the second distance L may be different than the first distance $L_0$. Using the first and second distances, the motion tracking apparatus may calculate a radial strain, e.g., based on the following equation:

$$\varepsilon = \frac{L - L_0}{L_0} \quad 4)$$

where the distance L and $L_0$ may be represented by respective vectors.

FIG. 9B shows an example of calculating a circumferential strain. As shown, the motion tracking apparatus may determine, based on a source image of the myocardium, a first (e.g., initial) distance $L_0$ in the circumferential direction of the myocardium that may correspond to a projection of the radial distance between two surface points of the myocardium in the source image. The surface points may be located on an inner surface $S_1$ (e.g., an endocardium) and an outer surface $S_2$ (e.g., an epicardium) of the myocardium, respectively (e.g., the surface points may be among the first plurality of points 108 and second plurality of points 110 shown FIG. 1, respectively). Then, in a target image of the myocardium, the motion tracking apparatus may locate the same two surface points used to determine the first distance $L_0$ and determine a second distance L in the circumferential direction of the myocardium that may correspond to a projection of the radial distance between the two surface points in the target image. Due to the motion of the myocardium from the source image to the target image, the surfaces $S_1$ and $S_2$ may have warped in the target image (e.g., as indicated by dotted lines in FIG. 9A), so the second distance L may be different than the first distance $L_0$. Using the first and second distances, the motion tracking apparatus may calculate a circumferential strain, e.g., based on Equation 4 shown above. The circumferential strain thus derived may include an endocardium circumferential strain (e.g., by projecting the radial distance onto the endocardium) that may represent a change in a circumferential length in the endocardium of myocardium. The circumferential strain thus derived may include an epicardium circumferential strain (e.g., by projecting the radial distance onto the epicardium) that may represent a change in a circumferential length in the epicardium of myocardium.

FIG. 9C shows an example of determining strain parameters (e.g., a radial strain and/or a circumferential strain) for different regions of a myocardium. As shown, the motion tracking apparatus may divide the myocardium into multiple regions (e.g., in accordance with a bullseye plot) and calculate strain parameters for each of the regions.

Each of the neural networks described herein may comprise multiple layers and each of the layers may correspond to a plurality of filters (e.g., kernels) having respective weights. The weights (e.g., the parameters described herein) may be learned through a training process that comprises inputting a large number of images from one or more training datasets to the neural networks, calculating differences or losses between a prediction result and a ground truth (e.g., based on a loss function such as MSE, L1/L2 norms, margin-based losses, etc.), and updating the weights assigned to the filters to minimize the differences or losses (e.g., based on a stochastic gradient descent of the loss function).

Figure 10:
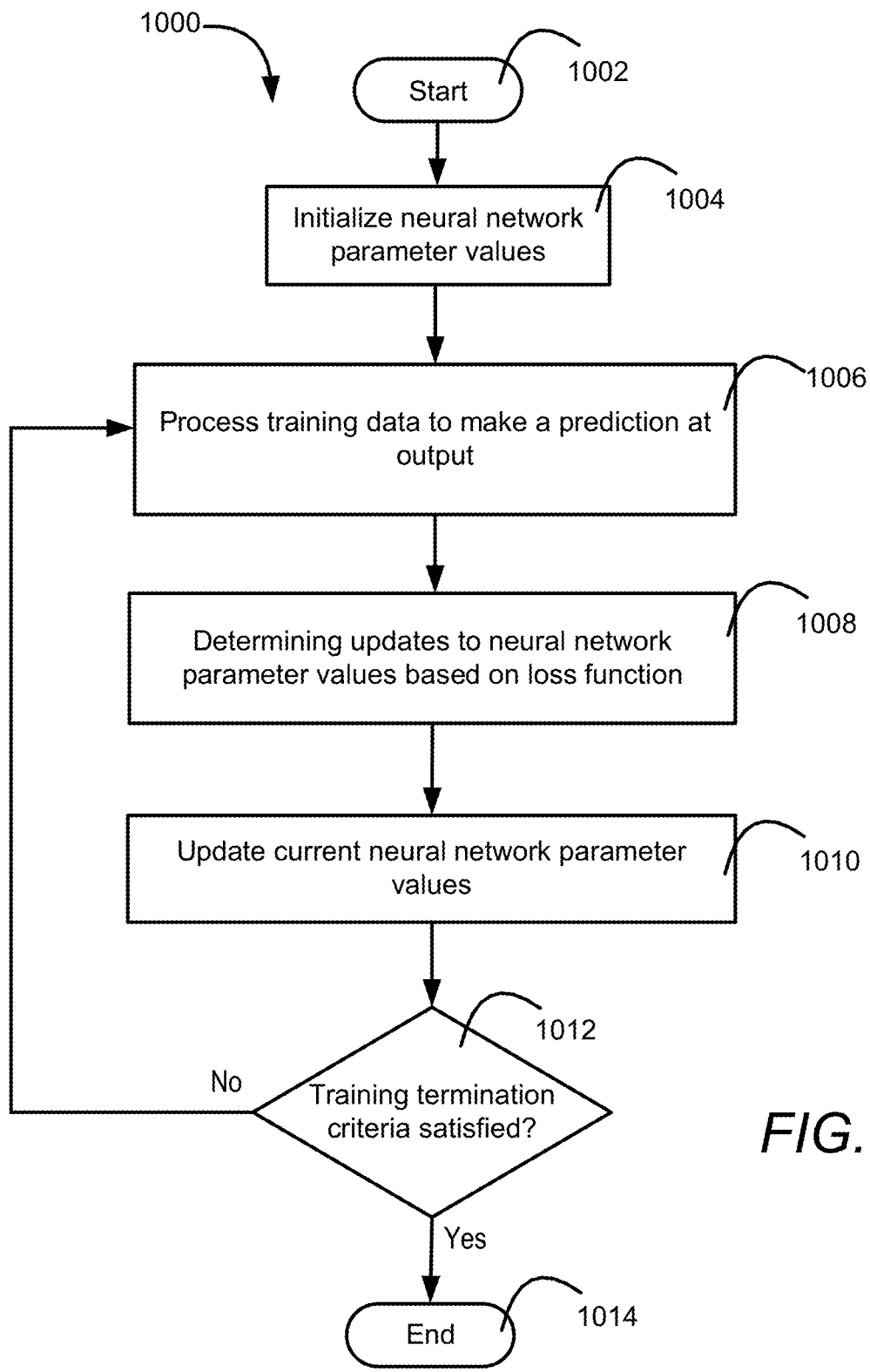
FIG. 10 is a flow diagram illustrating an example process for training a neural network described herein.

FIG. 10 is a flow diagram of an example process 1000 that may be implemented and executed during the training of a neural network described herein. The process 1000 may be performed by a system of one or more computers (e.g., one or more processors) located in one or more locations. The process 1000 may start at 1002 and, at 1004, the system may initialize the operating parameters of the neural network (e.g., weights associated with one or more layers of the neural network). For example, the system may initialize the parameters based on samples from one or more probability distributions or parameter values of another neural network with a similar architecture. At 1006, the system may process one or more training images using the parameter values currently assigned to the layers. A prediction may be made as a result of the processing and at 1008, the system may determine updates to the current parameter values, e.g., based on an objective or loss function and a gradient descent of the function. As described herein, the objective or loss function may be designed to minimize the difference between the prediction and an expected result (e.g., a ground truth). The objective function may be implemented using, for example, mean squared errors, L1 and/or L2 norms, etc. At 1010, the system may update the current values of the neural network parameters, for example, through a back-propagation process. At 1012, the system may determine whether one or more training termination criteria are satisfied. For example, the system may determine that the training termination criteria are satisfied if the system has completed a pre-determined number of training iterations, or if the change in the value of the loss function between two training iterations falls below a predetermined threshold. If the determination at 1012 is that the training termination criteria are not satisfied, the system may return to 1006. If the determination at 1012 is that the training termination criteria are satisfied, the system may end the training process 1000 at 1014.

Figure 11:
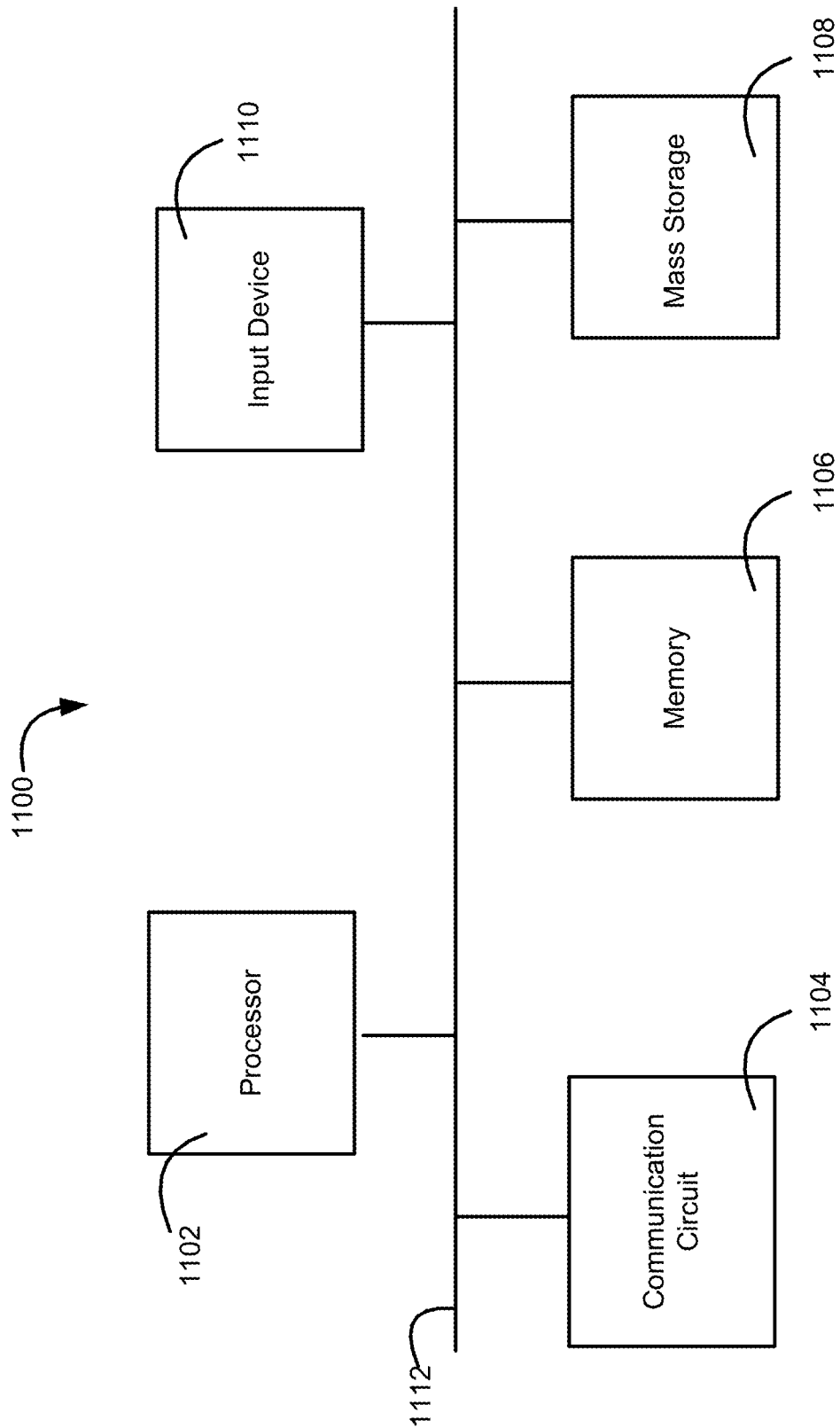
FIG. 11 is a block diagram illustrating example components of a motion tracking apparatus described herein.

The motion tracking apparatus described herein (e.g., such as the apparatus 300 in FIG. 3) may be implemented using one or more processors, one or more storage devices, and/or other suitable accessory devices such as display devices, communication devices, input/output devices, etc. FIG. 11 is a block diagram illustrating an example motion tracking apparatus 1100 as described herein. As shown, the motion tracking apparatus 1100 may include a processor (e.g., one or more processors) 1102, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The motion tracking apparatus 1100 may further include a communication circuit 1104, a memory 1106, a mass storage device 1108, an input device 1110, and/or a communication link 1112 (e.g., a communication bus) over which the one or more components shown in FIG.

11 may exchange information. The communication circuit 1104 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 1106 may include a storage medium configured to store machine-readable instructions that, when executed, cause the processor 1102 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 1108 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 1102. The input device 1110 may include a keyboard, a mouse, a voice-controlled input device, a touch sensitive input device (e.g., a touch screen), and/or the like for receiving user inputs to the motion tracking apparatus 1100.

It should be noted that the motion tracking apparatus 1100 may operate as a standalone device or may be connected (e.g., networked or clustered) with other computation devices to perform the functions described herein. And even though only one instance of each component is shown in FIG. 11, a skilled person in the art will understand that the motion tracking apparatus 1100 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example motion tracking apparatus is depicted and described herein with a specific order. It should be appreciated, however, that these operations may occur in various orders, concurrently, and/or with other operations not presented or described herein. And not all operations that the motion tracking apparatus is capable of performing are depicted and described herein, and not all illustrated operations are required to be performed by the apparatus.

For simplicity of explanation, the operation of the example apparatus or systems is depicted and described herein with a specific order. It should be appreciated, however, that these operations may occur in various orders, concurrently, and/or with other operations not presented or described herein. Furthermore, it should be noted that not all operations that a system or apparatus is capable of performing are depicted and described herein, and not all illustrated operations are required to be performed by the system or apparatus.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising one or more processors, wherein the one or more processors are configured to:
    obtain a source image of an anatomical structure and a target image of the anatomical structure;
    determine, in the source image, a first plurality of points on a first surface of the anatomical structure and a second plurality of points on a second surface of the anatomical structure, wherein the first plurality of points and the second plurality of points are determined based on a partial differential equation such that each point in the second plurality of points corresponds to a point in the first plurality of points;
    determine, based on the source image and the target image, a motion field that indicates a motion of the anatomical structure from the source image to the target image;
    estimate, based on the motion field and respective locations of the first plurality of points and the second plurality of points in the source image, respective locations of the first plurality of points and the second plurality of points in the target image;
    determine one or more strain parameters associated with the anatomical structure, wherein:
        the one or more strain parameters include at least one of a radial strain of the anatomical structure or a circumferential strain of the anatomical structure;
        if the one or more strain parameters include the radial strain, the radial strain is determined based on a change in a radial distance between one of the first plurality of points and one of the second plurality of points from the source image to the target image; and
        if the one or more strain parameters include the circumferential strain, the circumferential strain is determined based on a change in a circumferential distance from the source image to the target image, the circumferential distance being a projection of the radial distance in a circumferential direction of the anatomical structure.

2. The apparatus of claim 1, wherein the partial differential equation comprises Laplace's equation.

3. The apparatus of claim 2, wherein the first plurality of points and the second plurality of points are determined by solving Laplace's equation to determine one or more equal-potential surfaces and wherein each of the one or more equal-potential surfaces comprises at least one point from the first plurality of points and at least one point from the second plurality of points.

4. The apparatus of claim 1, wherein the first surface of the anatomical structure comprises an inner surface of the anatomical structure and the second surface of the anatomical structure comprises an outer surface of the anatomical structure.

5. The apparatus of claim 1, wherein the motion field is determined using one or more artificial neural networks and wherein the determination comprises deriving a first motion field based on respective features extracted from the source image and the target image, and refining the first motion field to obtain a refined motion field.

6. The apparatus of claim 5, wherein the refinement of the first motion field is performed by at least:
deriving a warped image based on the source image and the first motion field;
determining a second motion field based on respective features extracted from the warped image and the target image; and
combining the first motion field and the second motion field.

7. The apparatus of claim 1, wherein the source image of the anatomical structure comprises a source segmentation mask associated with the anatomical structure and wherein the target image of the anatomical structure comprises a target segmentation mask associated with the anatomical structure.

8. The apparatus of claim 1, wherein the one or more strain parameters include the radial strain of the anatomical structure, and wherein the one or more processors are configured to:
determine, in the source image, a first radial distance between a first point on the first surface of the anatomical structure and a second point on the second surface of the anatomical structure, wherein the first point belongs to the first plurality of points and the second point belongs to the second plurality of points, and wherein the first point corresponds to the second point in accordance with the partial differential equation;
determine, in the target image, a second radial distance between the first point on the first surface of the anatomical structure and the second point on the second surface of the anatomical structure;
determine a change between the first radial distance and the second radial distance; and
determine the radial strain based on the change between the first radial distance and the second radial distance.

9. The apparatus of claim 1, wherein the one or more strain parameters include the circumferential strain of the anatomical structure, and wherein the one or more processors are configured to:
determine, in the source image, a first circumferential distance in the circumferential direction of the anatomical structure that corresponds to a projection of a first radial distance in the source image between a first point and a second point that are respectively located on the first and second surfaces of the anatomical structure, wherein the first point and the second point are among the first plurality of points and the second plurality of points, respectively;
determine, in the target image, a second circumferential distance in the circumferential direction of the anatomical structure that corresponds to a projection of a second radial distance in the target image between the first point and the second point;
determine a change between the first circumferential distance and the second circumferential distance; and
determine the circumferential strain based on the change between the first circumferential distance and the second circumferential distance.

10. The apparatus of claim 1, wherein the anatomical structure comprises a myocardium.

11. A method for motion tracking and strain determination, the method comprising:
obtaining a source image of an anatomical structure and a target image of the anatomical structure;
determining, in the source image, a first plurality of points on a first surface of the anatomical structure and a second plurality of points on a second surface of the anatomical structure, wherein the first plurality of points and the second plurality of points are determined based on a partial differential equation such that each point in the second plurality of points corresponds to a point in the first plurality of points;
determining, based on the source image and the target image, a motion field that indicates a motion of the anatomical structure from the source image to the target image;
estimating, based on the motion field and respective locations of the first plurality of points and the second plurality of points in the source image, respective locations of the first plurality of points and the second plurality of points in the target image;
determining one or more strain parameters associated with the anatomical structure, wherein:
the one or more strain parameters include at least one of a radial strain of the anatomical structure or a circumferential strain of the anatomical structure;
if the one or more strain parameters include the radial strain, the radial strain is determined based on a change in a radial distance between one of the first plurality of points and one of the second plurality of points from the source image to the target image; and
if the one or more strain parameters include the circumferential strain, the circumferential strain is determined based on a change in a circumferential distance from the source image to the target image, the circumferential distance being a projection of the radial distance in a circumferential direction of the anatomical structure.

12. The method of claim 11, wherein the partial differential equation comprises Laplace's equation.

13. The method of claim 12, wherein the first plurality of points and the second plurality of points are determined by solving Laplace's equation to determine one or more equal-potential surfaces and wherein each of the one or more equal-potential surfaces comprises at least one point from the first plurality of points and at least one point from the second plurality of points.

14. The method of claim 11, wherein the first surface of the anatomical structure comprises an inner surface of the anatomical structure and the second surface of the anatomical structure comprises an outer surface of the anatomical structure.

15. The method of claim 11, wherein the motion field is determined using one or more artificial neural networks and wherein the determination comprises deriving a first motion field based on respective features extracted from the source image and the target image, and refining the first motion field to obtain a refined motion field.

16. The method of claim 15, wherein the refinement of the first motion field is performed by at least:
deriving a warped image based on the source image and the first motion field;
determining a second motion field based on respective features extracted from the warped image and the target image; and
combining the first motion field and the second motion field.

17. The method of claim 11, wherein the source image of the anatomical structure comprises a source segmentation mask associated with the anatomical structure and wherein the target image of the anatomical structure comprises a target segmentation mask associated with the anatomical structure.

18. The method of claim 11, wherein the one or more strain parameters include the radial strain of the anatomical structure and wherein determining the one or more strain parameters associated with the anatomical structure comprises:
- determining, in the source image, a first radial distance between a first point on the first surface of the anatomical structure and a second point on the second surface of the anatomical structure, wherein the first point belongs to the first plurality of points and the second point belongs to the second plurality of points, and wherein the first point corresponds to the second point in accordance with the partial differential equation;
- determining, in the target image, a second radial distance between the first point on the first surface of the anatomical structure and the second point on the second surface of the anatomical structure;
- determining a change between the first radial distance and the second radial distance; and
- determining the radial strain based on the change between the first radial distance and the second radial distance.

19. The method of claim 11, wherein the one or more strain parameters include the circumferential strain of the anatomical structure and wherein determining the one or more strain parameters associated with the anatomical structure comprises:
- determining, in the source image, a first circumferential distance in the circumferential direction of the anatomical structure that corresponds to a projection of a first radial distance in the source image between a first point and a second point that are respectively located on the first and second surfaces of the anatomical structure, wherein the first point and the second point are among the first plurality of points and the second plurality of points, respectively;
- determining, in the target image, a second circumferential distance in the circumferential direction of the anatomical structure that corresponds to a projection of a second radial distance in the target image between the first point and the second point;
- determining a change between the first circumferential distance and the second circumferential distance; and
- determining the circumferential strain based on the change between the first circumferential distance and the second circumferential distance.

20. The method of claim 11, wherein the anatomical structure comprises a myocardium.

* * * * *